(12) United States Patent
Early et al.

(10) Patent No.: US 6,437,565 B1
(45) Date of Patent: Aug. 20, 2002

(54) METHOD AND SYSTEM TO DETERMINE PHYSICAL PROPERTIES

(75) Inventors: Thomas Alan Early, Clifton Park; Elizabeth Anne Williams, Scotia; Bernadette Mondragon Bennett, Niskayuna, all of NY (US)

(73) Assignee: General Electric Company, Schenectady, NY (US)

( * ) Notice: Subject to any disclaimer, the term of this patent is extended or adjusted under 35 U.S.C. 154(b) by 27 days.

(21) Appl. No.: 09/614,048

(22) Filed: Jul. 11, 2000

(51) Int. Cl.[7] .................................................. G01V 3/00
(52) U.S. Cl. ..................... 324/309; 324/307; 324/312
(58) Field of Search ................................ 324/309, 312, 324/307, 314, 300

(56) References Cited

U.S. PATENT DOCUMENTS

| | | |
|---|---|---|
| 3,997,494 A | 12/1976 | Lever et al. |
| 4,694,252 A | 9/1987 | Riederer et al. ............ 324/309 |
| 4,894,416 A | 1/1990 | Gallucci ...................... 525/74 |
| 5,375,569 A | 12/1994 | Santella .................... 123/90.38 |
| 5,519,319 A | 5/1996 | Smith et al. ................. 324/306 |
| 5,786,411 A | 7/1998 | Barren et al. ................ 524/102 |
| 5,994,442 A | 11/1999 | Fujiguchi et al. ............ 524/417 |

OTHER PUBLICATIONS

Beall et al (chapter 4) in NMR Data Handbook for Biomedical Applications. Pergamon Press (1984), pp. 32–39.*
"A Guthausen et al., Analysis of Polymer Materials by Surface NMR via the Mouse", by A. Guthausen et al., Journal of Magnetic Resonance 130, 1–7 (1998).
"The Effect of Crosslinking in Elastomers Investigated by NMR Analysis of 13C Edited Transverse 1H NMR Relaxation, Macromolecular Chemistry, 197, 581–592 (1996)", Fullber et al,.

* cited by examiner

Primary Examiner—Edward Lefkowitz
Assistant Examiner—Brij B. Shrivastav
(74) Attorney, Agent, or Firm—Toan P. Vo; Noreen C. Johnson

(57) ABSTRACT

A method and system are provided that can be used at any stage of a manufacturing process to determine physical properties such as crosslink density. The method and system require little or no sample manipulation. The method and system are independent of rubber particle size and matrix composition. In the method and system, physical properties of a material are determined by NMR measurement. A $T_1$ (spin lattice relaxation time) is measured for a material, a $T_2$ (spin-spin relaxation time) is measured for the material and a value $T_1/T_2$ is calculated that is representative of a physical property of material.

44 Claims, 3 Drawing Sheets

METHOD AND SYSTEM TO DETERMINE PHYSICAL PROPERTIES

BACKGROUND OF THE INVENTION

The present invention relates to a method for determining a physical property of a material, particularly of an impact-modified plastic.

Rapid determination of a physical property of a plastic is an important capability for developing new materials, for monitoring manufacturing processes and for trouble-shooting customer service problems. Glass transition temperature, tensile strength, flexural modulus, flexural strength, notched IZOD and heat distortion temperature (HDT) are typically used to characterize performance and applicability of a plastic for a particular use. A number of features pertaining to the molecular structure of a plastic, including molecular weight, composition and chemical bonding affect these physical properties.

For this reason, considerable effort has been applied to develop methods to measure plastic molecular characteristics, particularly of rubber-modified plastics. These plastics are composite materials that comprise a rigid matrix characterized by a relatively high $T_g$ with a dispersed low $T_g$ rubbery phase. Composition of matrix and rubber, amount of dispersed rubber, particle size and particle size distribution of the rubber, strength of rubber-matrix adhesion and mechanical relaxation behavior of the rubber all influence the physical properties of these complex materials.

Mechanical relaxation is considered a key variable for optimizing effectiveness of a rubber as an impact modifier. Mechanical relaxation is strongly affected by crosslink density. Crosslink density is a quantitative measure of the number of crosslinks that exist in a given volume in a thermosetting polymer. Insufficiently crosslinked rubbers do not favorably impart toughness to a sufficient level, while over crosslinked rubbers are ineffective at retarding crack propagation.

Crosslink density in a polymer can be determined by pulsed Nuclear Magnetic Resonance (NMR) spectroscopy. Pulsed NMR techniques are used in instruments for the measurement of the type, property and quantity of lattice bound and free, magnetically active nuclei within a sample. Some of the substances and properties that have been measured by NMR techniques are: polymers and copolymers, oils, fats, crystalline materials and moisture, density and melt indices.

Pulsed NMR uses a burst or pulse of energy that is designed to excite the nuclei of a particular species of a sample being measured. the protons, or the like, of such sample having first been preprocessed in an essentially static magnetic field. In other words a precession is modified by the pulse. After the application of the pulse there occurs a free induction decay (FID) of the magnetization associated with the excited nuclei. That is, the transverse magnetization associated with the excited nuclei relaxes back to its equilibrium value of zero.

Several NMR procedures based on spin-spin relaxation time ($T_2$) have been developed for this purpose. A. Guthausen et al., "Analysis of Polymer Materials by Surface NMR via the MOUSE," Journal of Magnetic Resonance 130, 1–7 (1998) used $T_2$ to measure curing time and aging characteristics of a polyvinylidene difluoride. Füillber et al., "The effect of crosslinking in elastomers investigated by NMR analysis of $^{13}C$ edited transverse $^1H$ NMR relaxation," Macromolecular Chemistry 197, 581–583 (1996) correlated 'H spin—spin relaxation rate ($1/T_2$) to vulcameter torque.

There is a need for a method to measure crosslink density and other material properties in which little or no sample manipulation is required and that can be used at any stage of a manufacturing process

BRIEF SUMMARY OF THE INVENTION

According to the invention, a method is provided that can be used at any stage of a manufacturing process to determine a physical property such as crosslink density. The method requires little or no sample manipulation. The method is independent of rubber particle size and matrix composition. In the method, a physical property of a material is determined by NMR measurement. The method comprises measuring a $T_1$ (spin lattice relaxation time) for a material, measuring a $T_2$ (spin-spin relaxation time) for the material and calculating a value $T_1/T_2$ representative of a physical property of the material.

In another embodiment, the invention is a method to determine a physical property of a material, comprising deriving a model of a relationship between a physical property and a value $T_1/T_2$ of the material, detecting a signal $T_1$ and a signal $T_2$ of a sample of the material by NMR and comparing a quotient $T_1/T_2$ of the sample to the model to determine a physical property of the material.

In a final embodiment, the invention relates to a system to control a process to synthesize a material. The system comprises a processor, a detector and a comparator. The processor stores a model of a relationship between a physical property and a value $T_1/T_2$ of the material. The detector detects a signal $T_1$ and a signal $T_2$ of a sample of the material by NMR. The comparator compares a quotient $T_1/T_2$ of the sample to the model to determine a physical property of the material.

DETAILED DESCRIPTION OF THE INVENTION

According to the invention, standard NMR instrumentation is used to measure both $T_1$ (spin lattice relaxation time) and $T_2$ in a native sample. The invention is based on the observation that signals from a native sample are primarily due to a rubber impact modifier. An impact modifier such as polybutadiene gives multiple NMR signals. An unweighted $T_1$ and $T_2$ average can be determined for lines of all observed modifier resonances. The unweighted average is then used to calculate a $T_1/T_2$ ratio. The $T_1/T_2$ ratio correlates with physical property measurements.

Precession is the angular velocity of an axis of spin of a spinning rigid body, which arises as a result of external torque acting on the body. When a collection of nuclei are immersed in a magnetic field, each nucleus precesses with a characteristic frequency. In NMR, a collection of nuclei is irradiated with electromagnetic radiation of an appropriate frequency. Nuclear relaxation is caused by oscillating magnetic fields due to the relative motion of a neighboring magnetic nuclei. Relaxation parallel to an applied magnetic field can be characterized by the spin-lattice relaxation time $T_1$, which is produced by motion at or near the nuclear precession frequency (single quantum transition) and at or near twice the precession frequency (double quantum transition).

Relaxation perpendicular to a field can be characterized by the spin-spin relaxation time, $T_2$. Relaxation perpendicular to an applied magnetic field is sensitive to low frequency motion (zero quantum transition). A zero quantum transition results in no net change in bulk magnetization because one spin aligned parallel with an applied magnetic field exchanges magnetization with an adjacent spin, which is aligned anti-parallel to the applied field. A zero quantum transition has no net effect on $T_1$ relaxation. Since the zero quantum pathway is the only effective mechanism for spin-spin relaxation, $T_2$ is always smaller than $T_1$.

The Cycoloy® manufacturing process includes steps of polymerization of a core of a butadiene rubber (PBD) and grafting of styrene and acrylonitrile (SAN) to the PBD. The resulting grafted rubber is blended and extruded with PC, SAN copolymer and additives to a final formulation.

Figure 1:
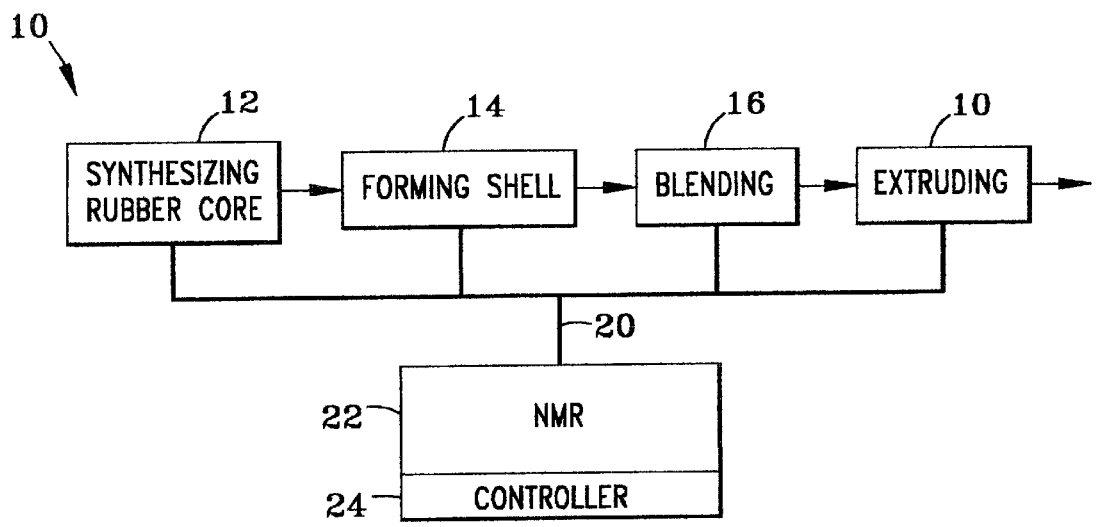
FIG. 1 is a schematic flow diagram of a method and system.

FIG. 1 is a schematic flow diagram of a method and system of the invention. In FIG. 1, a system and method 10 is shown to control a process to synthesize a material. The process can include steps of synthesizing a rubber core 12, forming a shell 14, blending 16 and extruding 18 to a powder, pellet or bar form. For example in one embodiment, the process is a Cycoloy® manufacturing process that includes steps of polymerization of a core 12 of a butadiene rubber (PBD) and grafting 14 of styrene and acrylonitrile (SAN) to the PBD. The resulting grafted rubber is blended 16 and extruded 18 with PC, SAN copolymer and additives to a final formulation.

During manufacturing, a Cycoloy® rubber increases in crosslink density. The extent of increase depends on process conditions and formulation. Crosslink density can also increase during the extrusion step. Crosslink density is a factor in determining physical properties and robustness of polymer blends. Hence it is important to monitor crosslink density of a PC/ABS blend during processing so as to monitor blend physical properties and robustness.

In the method of the present invention, a NMR experiment is first performed on a sample of a material during its processing. The NMR experiment uses a NMR apparatus having a NMR detector to detect NMR signals of the sample. The sample is positioned in a NMR test region of the NMR apparatus. A base magnetic field is applied to the sample to effect precession of nuclei of the sample. Then, the precession is modified resulting in NMR signals. Next, relaxation times $T_1$ and $T_2$ are derived from such NMR signals, which relaxation times are representative of a free induction decay of nuclei in the sample.

A controller, which can be a computer or microprocessor or the like, includes a processor to store a model of a relationship between a physical property and a value $T_1/T_2$ of the material. The controller also includes a comparator to compare a quotient $T_1/T_2$ of the sample to the model to determine a physical property of the material. The physical property can be any that is relatable to $T_1/T_2$ including crosslink density, glass transition temperature ($T_g$), flex strength, heat distortion temperature, notched IZOD, tensile strength and the like. The comparator compares quotient $T_1/T_2$ of the sample to a model of crosslink density for the material being process to identify the crosslink density of the sample.

These and other features will become apparent from the following detailed discussion, which by way of example without limitation describe preferred embodiments of the present invention.

In the Examples, samples in powder, pellet or bar form were run on a GE NMR Instruments Omega 300 MHz solids spectrometer operating at 300.54 MHz or an Omega 300 MHz liquids spectrometer operating at 300.1 MHz, for $^1$H except for Noryl® samples, which were run on a GE Instruments QE 300 operating at 300.1 MHz. No sample preparation was required, except for insuring that the sample would fit into a standard 5mm NMR spinner or tube. Molded parts were examined by excising small pieces to insert into the tube or spinner.

Probes were tuned for optimal sample sensitivity and ninety degree pulse time was checked on a typical sample. $T_1$ data were obtained using a standard 180°-τ-90° inversion recovery pulse sequence and $T_2$ data were obtained with a standard 90°-τ/2-180°-τ/2 Hahn spin echo pulse sequence where the τ value is an $^1$H chemical shift scale. Sixteen scans each at a pulse repetition time of 3s were conducted for each τ value.

Ten different τ values were obtained (at 10 ms, 20 ms, 50 ms, 100 ms 160 ms 250 ms 400 ms, 630 ms, 1 s and 1.5 s) with five replicates at 10 ms, 50 ms, 160 ms, 400 ms and 1 s for a total of fifteen τ values for each $T_1$ experiment. Eight different τ values are obtained (at 200 ms, 360 ms, 640 ms, 1.12 ms, 2 ms, 3.6 ms 6.4 ms and 11.2 ms) with four replicates at 200 ms, 640 ms, 2 ms and 6.4 ms for a total of twelve τ values for each $T_2$ experiment. The τ values were run in a random order (according to TABLE 1 to eliminate systematic errors due to instrument drift.

TABLE 1

| $T_1$ | $T_2$ |
|---|---|
| 10 ms | 640 us |
| 400 ms | 3.6 ms |
| 160 ms | 6.4 ms |
| 250 ms | 200 us |
| 50 ms | 11.2 ms |
| 10 ms | 360 us |
| 160 ms | 1.12 ms |
| 100 ms | 200 us |
| 1.5 s | 2 ms |
| 1 s | 2 ms |
| 50 ms | 640 us |
| 630 ms | 6.4 ms |
| 1 s | |
| 400 ms | |
| 20 ms | |

The value pairs were then fit through an iterative procedure to minimize residual error. $T_1$ data were fit to an expression, $A=A_0[1-(W+1)e^{-\tau/T_1}]$ where A is measured intensity (y) at a relaxation delay of τ(x), $A_0$ is a calculated intensity at full relaxation and W is a calculated fractional inversion, which is within a few percent of 1.00 in all cases. $T_2$ x–y values are fit to the equation $A=A=_0e^{-\tau/T_2}$. The $T_1/T_2$ is then calculated from the best fit values of $T_1$ and $T_2$.

A GE NMR Instruments Omega 300 MHz spectrometer with an offset of 7.22 ppm for observe frequency was used to obtain $^1$H spectra data for solid samples. A sweep width of 20.0 kHz was used with 8 k data points resulting in an acquisition time of 409.6 ms. A GE NMR Instruments Omega 300 MHz spectrometer with an off set of 6.70 ppm for observe frequency was used to obtain $^1$H spectra data for liquid samples. A 20.0 KHz sweep width was used with 256 data points, which resulted in an acquisition time of 12.8 ms.

EXAMPLE 1

Figure 2:
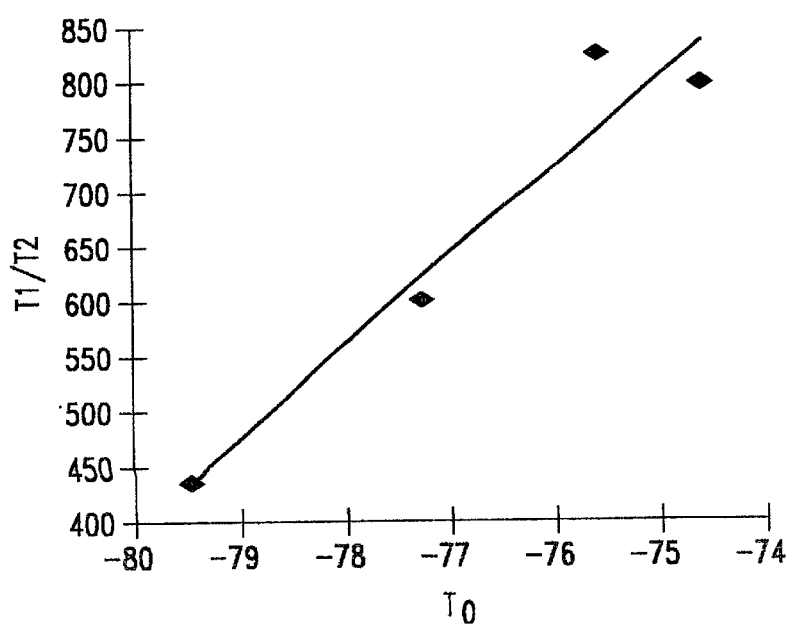
FIG. 2 is a plot of $T_1/T_2$ and $T_g$.

NMR measurements were made on a series of standard polymers that had been chemically crosslinked with peroxide. These polymers varied in glass transition temperature ($T_g$) from −79.5 to −74.8° C. as crosslink density increased with higher peroxide levels. The standard deviation for the measurements was 4.1 units. Subsequently, the standard deviation was improved to 1.7 by carrying out the measurements on the liquid spectrometer rather than the solid state spectrometer. FIG. 2 shows a correlation between ratio of the proton NMR relaxation $T_1/T_2$ and $T_g$. A one degree change in $T_g$ resulted in a corresponding $T_1/T_2$ change of approximately 75 units.

EXAMPLE 2

PC/ABS (Cycoloy®)

Cycoloy® is a blend of PC and ABS. In a Cycoloy® manufacturing process, butadiene is polymerized, a resulting polybutadiene rubber is agglomerated and styrene and acrylonitrile are simultaneously polymerized and grafted to the rubber. The resulting grafted rubber is blended with PC and SAN and extruded to form a Cycoloy® blend. Samples in this study contained levels of butadiene rubber in the high rubber graft loading range. The rubber levels were either 13% or 21% with a particle size of either 210 or 280 nm. The SAN molecular weights were either 60K or 100K. Rubber crosslink density was controlled by using either 0.6 or 0.4 parts t-dodecylmercaptan chain transfer agent.

NMR measurements were made on samples of grafted rubber at the two levels of rubber and two levels of particle size. These samples were designated HRGs. In this application, an HRG is a high rubber graft copolymer prepared by grafting a styrene-acrylonitrile copolymer onto a butadiene rubber. See Barren et al., U.S. Pat. No. 5,786,411. The HRGs were then used to prepare Cycoloy® pellets and Cycoloy® samples molded under "normal" molding conditions (255° C. for 3 min) and "abusive" molding conditions (300° C. for 15 min).

The following four groups of samples were examined: (1) four (4) HRGs used to prepare Cycoloy samples, (2) Cycoloy pellets, (3) samples molded under normal conditions and (4) samples molded under abusive conditions. Rubber crosslink density is known to increase through this sequence. Results are shown in the following TABLE 2. In the TABLE 2, particle size is in nanometers, crosslink density is in parts mercaptan, HRG loading is in percent and SAN Mol. Wt. is MW/1000. Particle size and crosslink density refer to the HRG. The HRG loading and SAN Mol. Wt. refer to the Cycoloy® pellet and molded blends.

TABLE 2

| Sample Series | Sample | Particle Size | Crosslink Density | HRG Loading | SAN Mol. Wt. | T1/T2 |
|---|---|---|---|---|---|---|
| II | HRG | 210 | 0.6 | | | 277 |
| | Cycoloy Pellets | | | 13 | 110 | 237 |
| | Cycoloy Normal Mold | | | 13 | 110 | 535 |
| | Cycoloy Abusive Mold | | | 13 | 110 | 988 |
| II | HRG | 280 | 0.6 | | | 307 |
| | Cycoloy Pellets | | | 13 | 60 | 269 |
| | Cycoloy Normal Mold | | | 13 | 60 | 478 |
| | Cycoloy Abusive Mold | | | 13 | 60 | 981 |
| III | HRG | 210 | 0.4 | | | 363 |
| | Cycoloy Pellets | | | 13 | 60 | 375 |
| | Cycoloy Normal Mold | | | 13 | 60 | 616 |
| | Cycoloy Abusive Mold | | | 13 | 60 | 1044 |
| IV | HRG | 280 | 0.4 | | | 336 |
| | Cycoloy Pellets | | | 13 | 110 | 324 |
| | Cycoloy Normal Mold | | | 13 | 110 | 659 |
| | Cycoloy Abusive Mold | | | 13 | 110 | 1077 |
| V | HRG | 210 | 0.6 | | | 277 |
| | Cycoloy Pellets | | | 21 | 60 | 249 |
| | Cycoloy Normal Mold | | | 21 | 60 | 548 |
| | Cycoloy Abusive Mold | | | 21 | 60 | 961 |
| VI | HRG | 280 | 0.6 | | | 307 |
| | Cycoloy Pellets | | | 21 | 110 | 303 |
| | Cycoloy Normal Mold | | | 21 | 110 | 613 |
| | Cycoloy Abusive Mold | | | 21 | 110 | 1136 |
| VII | HRG | 210 | 0.4 | | | 363 |
| | Cycoloy Pellets | | | 21 | 110 | 416 |
| | Cycoloy Normal Mold | | | 21 | 110 | 743 |
| | Cycoloy Abusive Mold | | | 21 | 110 | 1128 |
| VIII | HRG | 29− | 0.4 | | | 336 |
| | Cycoloy Pellets | | | 21 | 60 | 315 |
| | Cycoloy Normal Mold | | | 21 | 60 | 619 |
| | Cycoloy Abusive Mold | | | 21 | 60 | 994 |

For HRGs with higher crosslink density (III and IV), the sample with the larger particle size (IV) had a slightly lower $T_1/T_2$ value (but within experimental error) whereas for the HRGs with lower crosslink density (I and II), the sample with the larger particle size (II) had a slightly higher $T_1/T_2$ value (but again within experimental error). Hence, it was concluded that particle size does not affect $T_1/T_2$ values. Additionally, samples of PC and SAN run under the same conditions as those for the HRG and Cycoloy® samples of TABLE 2 indicated that background signals from the matrix polymer do not contribute to $T_1/T_2$.

Comparison examination of pellets, normally molded bars and abusively molded bars showed an expected increase in $T_1/T_2$ as crosslinking increased. A comparison of HRG samples with respective Cycoloy® pellets, indicates that $T_1/T2$ remains the same or drops slightly (counter to the expectation that the crosslink density should increase during extrusion and therefore $T_1/T_2$ should also increase). However, extraction of Cycoloy phases and determination of $T_1/T_2$ for the phases established that the decrease was due to a phase triaxial tension effect and that $T_1/T_2$ is sensitive and relatable to the state of the rubber in the matrix.

EXAMPLE 3

Figure 3:
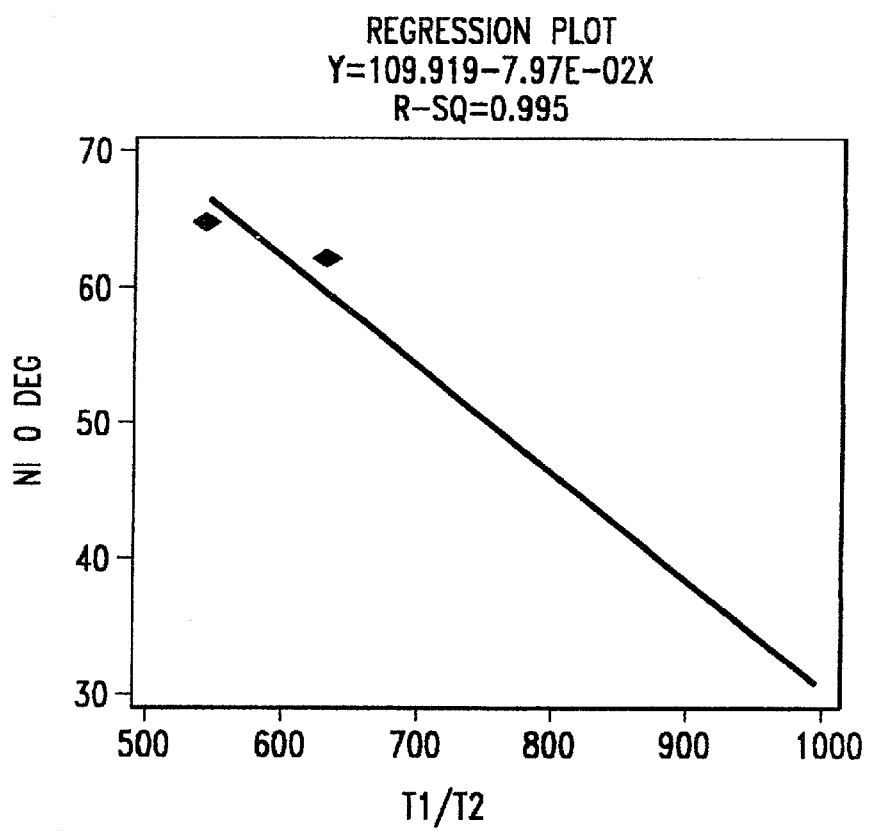
FIG. 3 is a plot of notched IZOD and $T_1/T_2$.

Rubber crosslink density is a major factor in determining impact strength. Molecular weight and HRG loading also strongly affect this physical property. In this Example, four separate sets of data were generated with molecular weight and HRG loading held constant within each set. FIG. 3 is a plot of notched IZOD at 0°C. and $T_1/T_2$ for two each of normally molded bars and abusively molded bars with low SAN molecular weight and with high HRG loading. In the graph, IZOD values are in ft.lb/inch. A regression analysis correlation coefficient ($R^2$) was 0.995 indicating that $T_1/T_2$ was a measure of rubber crosslink density in these materials. The correlation coefficient for high SAN molecular weight and HRG loading samples was 0.937. The correlation coefficient for a series with low SAN molecular weight and low HRG loading was 0.944 and the correlation coefficient for a series with high SAN molecular weight and low HRG loading was 0.986.

EXAMPLE 4

Glass-Filled Noryl®

Samples of 20% glass filled Noryl(g thermoplastic resin (a poly(2,6-dimethyl-1,4-phenylene) ether (PPE) (weight average molecular weight 64,000, number average molecular weight 22,000)) from General Electric Company were incorporated into 50/50 blends with a rubber modified high impact polystyrene (HIPS). The blends were molded into a standard ASTM test tree shape on a Van Dorn 120 ton molding machine. Analytical samples were cut from the shapes. Molding barrel temperatures (350°, 365° and 389° C.) and residence times (2, 5, 10 and 15 min) were varied.

A 290–310° C. molding temperature range is recommended for glass-filled Noryl®. A 330° C. temperature is considered abusive especially at longer residence times. A GE NMR Instruments Omega 300 MHz spectrometer was used to conduct NMR experiments on the samples as described above. Gel permeation chromatography (GPC) was used to establish PPE molecular weight. Physical properties, including tensile strength, flexural modulus, flexural strength, notched IZOD and heat distortion temperature (HDT) were measured, and correlations with analytical measurements were examined.

No statistically significant change in PPE molecular weight was detected by GPC as molding conditions were varied, indicating that the polymer did not degrade. $T_1/T_2$ correlated well with processing conditions ($R^2$ 97.6% and 94.2% respectively). Temp, Time*Time, Time*Temp were critical factors in the correlation expression.

Changes in physical properties of the materials were relatively small, suggesting that the materials were very robust with respect to abusive molding. Tensile strength, flex strength, and flex modulus all increased with increasing time and temperature. At the most abusive conditions, HDT and notched IZOD dropped. All changes in physical properties were consistent with increasing rubber crosslinking with higher molding temperatures and longer residence times.

Figure 4:
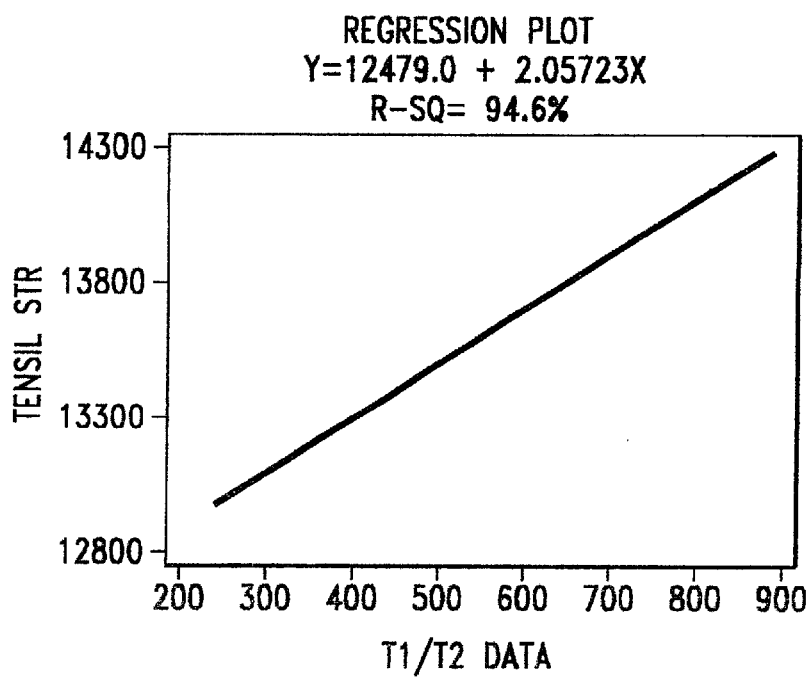
FIG. 4 is a plot of tensile strength vs. $T_1/T_2$.

The $T_1/T_2$ NMR method was applied to provide information on properties of the molded materials. Improved correlations were found with $T_1/T_2$. The poorest correlation was between $T_1/T_2$ and flex strength ($R^2$=77.4%) and the best correlations with $T_1/T_2$ were for HDT (92.9%), notched IZOD (93.6%) and tensile strength (94.6%). These data are shown in TABLE 3. A plot of tensile strength vs. $T_1/T_2$ is shown in FIG.4.

TABLE 3

| Property | $R^2$ with $T_1/T_2$ (%) |
|---|---|
| Tensile Strength | 94.6 |
| Flexural Modulus | 81.6 |
| Flexural Strength | 71.2 |
| Notched Izod | 93.0 |
| Heat Distortion Temp. | 90.6 |

EXAMPLE 5

SIM/SAN

SIMs are silicone rubber core/shell impact modifiers. In this example, SIM modifiers were made by first synthesizing submicron silicone latex particles by a conventional emulsion polymerization process using, octamethylcyclotetrasiloxane ($D_4$) as a monomer, tetraethoxysilane (TEOS) as a crosslinker, and γ-methacryloxy-propylmethyldimethoxysilane (MAPDMMS) as a graft crosslinker. The silicone particles were swelled with butyl acrylate (BA) monomer mixture (with allyl methacrylate as crosslinking agent) at a ratio of 70/30 silicone/BA and then polymerized by a batch process. The SIM was produced by a semi-continuous emulsion polymerization of styrene and acrylonitrile (S/AN 75/25) in the presence of silicone/BA core particles to produce a silicone/BA core and SAN shell at a 1:1 ratio of core to shell.

SIM samples were coagulated, cleaned, dried and then blended at 27 wt % with SAN. The blends were then extruded to pellets by means of a Welding Engineer 20 mm twin-screw extruder at 230° C. set temperature, 400 rpm, and 15–17 lbs/hour throughput. The pellets were injection molded to test specimens with an Engel 30 Ton Injection Molder.

Figure 5:
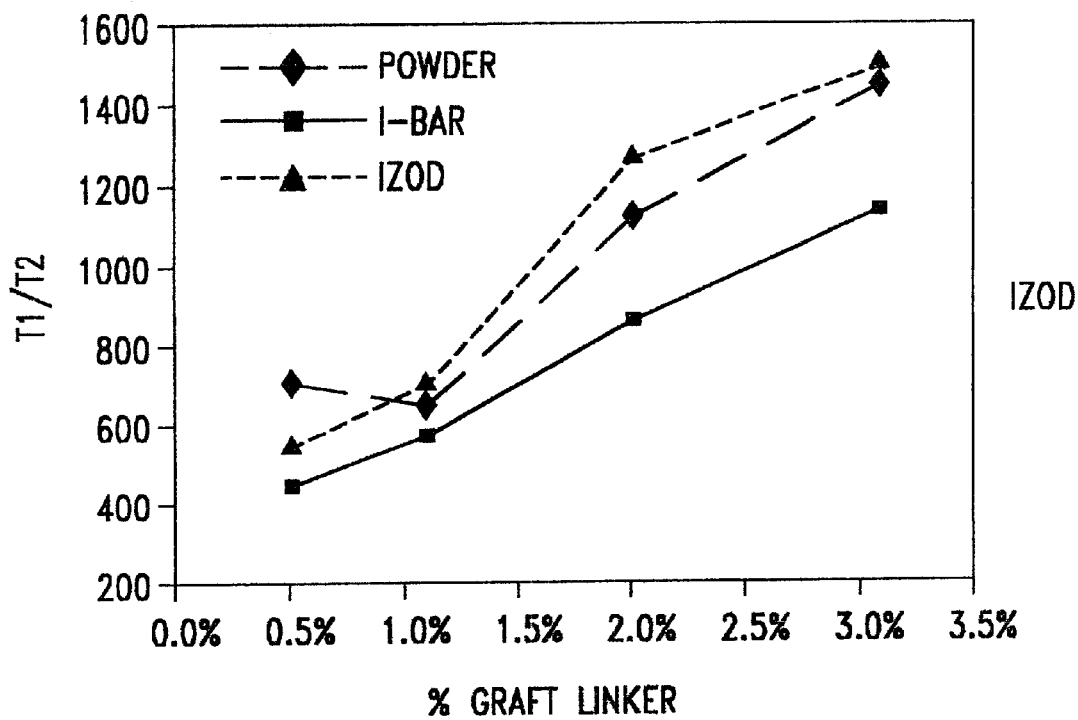
FIG. 5 is a plot of $T_1/T_2$ and crosslinker.

The $T_1/T_2$ method was applied to a series of SIM/SAN samples that were prepared with different levels of graft crosslinker (MAPDMMS). With this material, proton spectra are dominated by the SIM impact modifier. The SAN phase is mostly unobservable. $T_1/T_2$ values were derived from data on powdered and I-bar samples. The bars were also subjected to IZOD impact tests carried out following ASTM D256 with a 2 lb hammer. Results are shown in FIG. 5.

The SIM/SAN samples showed increasing $T_1/T_2$ value with increasing crosslink density. The $T_1/T_2$ value correlated well with IZOD impact strength. With the SIM/SAN samples, processing decreased $T_1/T_2$ indicating that the silicone rubber molecular weight degraded.

EXAMPLE 6

ASA/SAN

ASA is a core/shell impact modifier with a polybutylacrylate (PBA) core and styrene-acrylonitrile polymer shell. ASA/SAN was synthesized by first preparing PBA rubber particles with a bimodal particle size distribution (about 130 nm and about 650 nm) with different levels of dicyclopentenyloxyethylmethacrylate (DCPOMA) crosslinker. A small amount of α-methyl styrene dimer was added to the PBA particles to study the effect on swell index and consequently, impact performance. Next, a SAN polymer (S/AN 50/50) was grafted by emulsion polymerization onto the PBA rubber core to form a shell layer with a 1/1 core/shell ratio.

The ASA samples were coagulated, cleaned, dried and then blended at 27 wt % with SAN. The samples were then extruded to pellets by means of a Welding Engineer 20 mm twin-screw extruder at 230° C. set temperature, 400 rpm, and 15–17 lbs/hour throughput. The pellets were injection molded to test specimens with an Engel 30 Ton Injection Molder.

Figure 6:
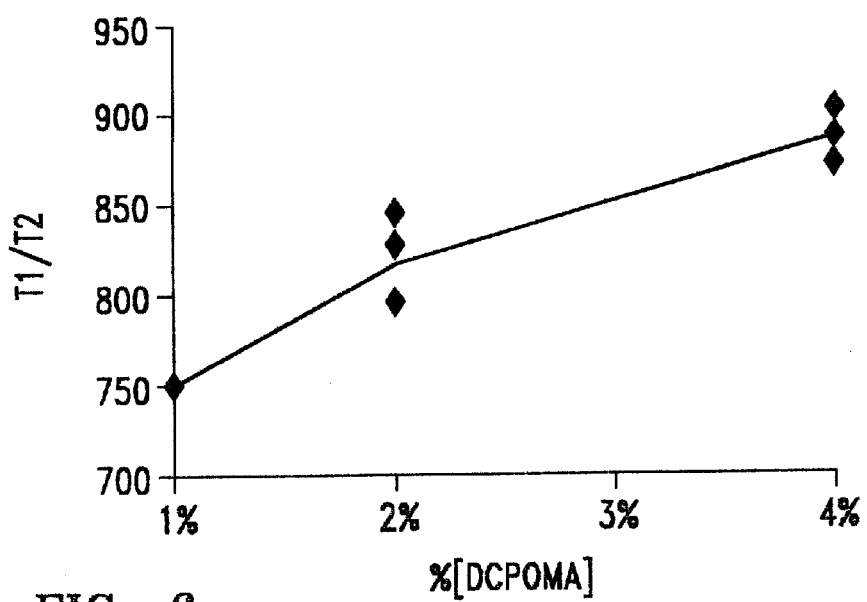
FIG. 6 is a plot of $T_1/T_2$ of polybutylacrylate (PBA) and crosslinker

FIG. 6 shows $T_1/T_2$ value of PBA resonance plotted against level of crosslinking agent, DCPOMA. The solid line shows an average value for each of 1%, 2% and 4% crosslinker concentrations. Again with this system, $T_1/T_2$ correlated with rubber impact modifier crosslink density.

The Examples show that the $T_1/T_2$ is effective for measuring relative rubber crosslink density in Cycoloy®, glass filled Noryl®, SIM/SAN blends and ASA/SAN blends. The $T_1/T_2$ method requires little or no additional sample preparation and measurements can be performed in as short a period as twenty minutes. Analysis of data indicates that $T_1/T_2$ is a sensitive probe into the state of rubber in a Cycoloy® blend. The $T_1/T_2$ value is independent of rubber particle size and is not affected by matrix interference.

While preferred embodiments of the invention have been described, the present invention is capable of variation and modification and therefore should not be limited to the precise details of the Examples. The invention includes changes and alterations that fall within the purview of the following claims.

What is claimed is:

1. A method for determining at least one physical property of a material by NMR measurement, said method comprising:
    determining a spin lattice relaxation time ($t_1$) for said material;
    determining a spin-spin relaxation time ($t_2$) for said material;
    calculating a ratio $t_1/t_2$; and
    determining said at least one physical property of said material by relating said ratio to known values of said at least one physical property.

2. The method of claim 1, wherein said spin-lattice relaxation time represents a relaxation parallel to an applied magnetic field.

3. The method of claim 1, wherein said spin-spin relaxation time represents a relaxation time perpendicular to an applied magnetic field.

4. The method of claim 1, wherein said NMR measurement comprises:
    positioning a sample of said material in an NMR test region;
    applying a base magnetic field to said sample to effect precession of nuclei of said sample;
    modifying the precession; and
    detecting a resulting relaxation signal $T_1$ and signal $T_2$ representative of a free induction decay of nuclei of said sample.

5. The method of claim 1, wherein said physical property is crosslink density.

6. The method of claim 1, wherein said physical property is the glass transition temperature ($T_g$).

7. The method of claim 1, wherein said physical property is flex strength.

8. The method of claim 1, wherein said physical property is heat distortion temperature.

9. The method of claim 1, wherein said physical property is notched IZOD.

10. The method of claim 1, wherein said physical property is tensile strength.

11. The method of claim 1, wherein said material is a plastic.

12. The method of claim 1, wherein said material is a polycarbonate/acrylonitrile-butadiene-styrene resin blend.

13. The method of claim 1, wherein the material sample is a rubber, unweighted $T_1$ and $T_2$ averages are determined for resonances and said unweighted averages are used to calculate said $T_1/T_2$ ratio.

14. The method of claim 1, comprising obtaining said $T_1$ with a 180°-τ-90° inversion recovery pulse sequence.

15. The method of claim 1, comprising obtaining said $T_2$ with a 90°-τ/2-180°-τ/2 inversion recovery pulse sequence.

16. The method of claim 1, comprising measuring more than one $T_1$ value and applying an iterative procedure to obtain said $T_1$ used to calculate said $T_1/T_2$.

17. The method of claim 16, wherein said iterative procedure comprises fitting $T_1$ values to the expression $A=A^0[1-(W+1)e^{31\ 1/\tau 1}]$ where τ is an $^1$H chemical shift scale, A is measured intensity at a relaxation delay of τ, $A_0$ is a calculated intensity at full relaxation and W is a calculated fractional inversion of an approximate value of 1.

18. The method of claim 1, comprising measuring more than one $T_2$ value and applying an iterative procedure to obtain said $T_2$ used to calculate said $T_1/T_2$.

19. The method of claim 18, wherein said iterative procedure comprises fitting $T_2$ values to the expression $A=A_0e^{-1/\tau 2}$ where τ is an $^1$H chemical shift scale, A is measured intensity at a relaxation delay of τ and $A_0$ is a calculated intensity at full relaxation.

20. A method for determining a physical property of a material, said method comprising:
    deriving a model of a relationship between values of a physical property and values of $T_1/T_2$ of predetermined first samples of said material, wherein $T_1$ is spin lattice relaxation time measured by NMR and $T_2$ is spin-spin relaxation time measured by NMR, and wherein said first samples have been produced so to have a range of said values of said physical property;
    obtaining $t_1$ and $t_2$ of a second sample of said material by performing a NMR experiment on said second sample that has an unknown value of said physical property, wherein $t_1$ is spin lattice relaxation time and $t_2$ is spin-spin relaxation time of said second sample; and
    applying a value of a quotient $t_1/t_2$ to said model to determine a physical property of said second sample.

21. The method of claim 20, wherein said sample is taken during a processing of said material and said processing is controlled according to said physical property of said material.

22. The method of claim 20, wherein said sample is taken during a processing of said material and conditions of said processing are adjusted according to said physical property of said material.

23. The method of claim 22, further comprising establishing target properties for a product of said processing and adjusting conditions of said processing according to said physical property of said material to produce a product characterized by said target property.

24. The method of claim 20, wherein said sample is taken during a processing of said material comprising synthesizing a rubber core, forming a shell, blending to form an extrudable composition and extruding said composition.

25. The method of claim 20, comprising detecting said signal $T_1$ and signal $T_2$ by positioning said sample in an NMR test region;

applying a base magnetic field to the sample to effect precession of nuclei of said sample;

modifying the precession; and detecting a resulting relaxation signal $T_1$ and signal $T_2$ representative of a free induction decay of nuclei of said sample.

26. The method of claim 20, wherein said physical property is crosslink density.

27. The method of claim 20, wherein said physical property is the glass transition temperature ($T_g$).

28. The method of claim 20, wherein said physical property is flex strength.

29. The method of claim 20, wherein said physical property is heat distortion temperature.

30. The method of claim 20, wherein said physical property is notched IZOD.

31. The method of claim 20, wherein said physical property is tensile strength.

32. The method of claim 20, wherein said material is a plastic.

33. The method of claim 20, wherein said material is a polycarbonate/acrylonitrile-butadiene-styrene resin blend.

34. The method of claim 20, wherein the material sample is a rubber, unweighted $T_1$ and $T_2$ averages are determined for resonances and said unweighted averages are used to calculate said $T_1/T_2$ ratio.

35. The method of claim 20, comprising obtaining said $T_1$ with a 180°-τ-90° inversion recovery pulse sequence.

36. The method of claim 20, comprising obtaining said $T_2$ with a 90°-τ/2-180°-τ/2 inversion recovery pulse sequence.

37. The method of claim 20, comprising measuring more than one $T_1$ value and applying an iterative procedure to obtain said $T_1$ used to calculate said $T_1/T_2$.

38. The method of claim 37, wherein said iterative procedure comprises fitting $T_1$ values to the expression $A=A_0[1-(W+1)e^{-1/\tau 1}]$ where τ is an $^1H$ chemical shift scale, A is measured intensity at a relaxation delay of τ, $A_0$ is a calculated intensity at full relaxation and W is a calculated fractional inversion of an approximate value of 1.

39. The method of claim 20, comprising measuring more than one $T_2$ value and applying an iterative procedure to obtain said $T_2$ used to calculate said $T_1/T_2$.

40. The method of claim 39, wherein said iterative procedure comprises fitting $T_2$ values to the expression $A=A_0e^{-1/\tau}$ where τ is an $^1H$ chemical shift scale, A is measured intensity at a relaxation delay of τ and $A_0$ is a calculated intensity at full relaxation.

41. A system to control a process to synthesize a material, said system comprising:

a processor to store a model of a relationship between values of a physical property and values of $T_1/T_2$ of predetermined first samples of said material, wherein $T_1$ is spin lattice relaxation time measured by NMR and $T_2$ is spin-spin relaxation time measured by NMR, and wherein said first samples have been produced so to have a range of said values of said physical property;

a detector to detect NMR signals of a second sample of said material that has an unknown value of said physical property, said NMR signals being converted to $t_1$ and $t_2$, wherein $t_1$ is spin lattice relaxation time and $t_2$ is spin-spin relaxation time of said second sample; and a comparator to determine a physical property of said second sample by relating a quotient $t_1/t_2$ to said physical property through said model, said physical property of said second sample being used to control said process.

42. The system of claim 41, additionally comprising a controller to control said process according to said physical property of said material.

43. The system of claim 41, additionally comprising a controller to adjust conditions of said process according to said physical property of said material.

44. The system of claim 41, additionally comprising a controller to store a model of a target property for a product of said process and to adjust conditions of said process according to a comparison of said physical property of said material and said target property.

* * * * *